(12) United States Patent
Medintz et al.

(10) Patent No.: US 8,512,755 B2
(45) Date of Patent: Aug. 20, 2013

(54) COMPACT MULTIFUNCTIONAL LIGAND TO ENHANCE COLLOIDAL STABILITY OF NANOPARTICLES

(75) Inventors: Igor L. Medintz, Springfield, VA (US); Kimihiro Susumu, Alexandria, VA (US); Michael H. Stewart, Springfield, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 51 days.

(21) Appl. No.: 13/209,974

(22) Filed: Aug. 15, 2011

(65) Prior Publication Data

US 2013/0045499 A1 Feb. 21, 2013

(51) Int. Cl.
| | |
|---|---|
| C07D 339/04 | (2006.01) |
| C07D 293/00 | (2006.01) |
| C07D 285/16 | (2006.01) |
| C07D 487/00 | (2006.01) |
| A61K 9/14 | (2006.01) |

(52) U.S. Cl.
USPC .................. 424/489; 544/1; 544/7; 532/1

(58) Field of Classification Search
None
See application file for complete search history.

(56) References Cited

U.S. PATENT DOCUMENTS

| | | | | |
|---|---|---|---|---|
| 5,310,648 | A * | 5/1994 | Arnold et al. ............... | 435/5 |
| 2003/0044402 | A1 | 3/2003 | Nelson | |
| 2010/0267967 | A1 | 10/2010 | Stewart et al. | |

FOREIGN PATENT DOCUMENTS

| | | | |
|---|---|---|---|
| CN | 1504186 A * | 6/2004 | |
| WO | 2009-108168 A2 | 9/2009 | |
| WO | 2011-084710 A1 | 7/2011 | |

OTHER PUBLICATIONS

Karube, Y., et al., "Radioactive metal complexes with affinity for tumors. II. Biodistribution of radioactivity in cellular and subcellular fractions of tumor tissues", 1989, Chem Pharm Bull, Abstract, p. 1.*
Cho, YK., et al., "The hemostatic effect of endoscopic sodium hyaluronate injection in peptic ulcer bleeding.", 2007, Hepatogastroenterology, Abstract, p. 1-2.*
CN1504186 translation, Cnet translation of CN1504186, printed Mar. 15, 2013, pp. 1-4.*
Nam,,J., et al., "pH-Induced Aggregation of Gold Nanoparticles for Photothermal Cancer Therapy", 2009, JACS, pp. 13639-13645.*
Bhang, S.H., et al., "Hyaluronic Acid—Quantum Dot Conjugates for In Vivo Lymphatic Vessel Imaging", 2009, ACS NANO, p. 1389-1398.*
Algar et al., Bioconjugate Chem. 2011, 22, 825-858 (2011).
Oh, Eunkeu; Kimihiro Susumu; Ramasis Goswami and Hedi Mattoussi, "One-Piece Synthesis of Water-Soluble Gold Nanoparticles with Control over Size and Surface Functionalities", Langmuir, 2010, ASAP article.
Mattoussi H, Mauro JM, Goldman ER, Anderson GP, Sundar VC, Mikulec FV, Bawendi MG Self-assembly of CdSe-ZnS quantum dot bioconjugates using an engineered recombinant protein. J Am. Chem. Soc. 2000, 122, 12142-12150.
Medintz, Igor L.; Thomas Pons; James B. Delehanty; Kimihiro Susumu; Florence M. Brunel; Philip E. Dawson; and Hedi Mattoussi, "Intracellular Delivery of Quantum Dot—Protein Cargos Mediated by Cell Penetrating Peptides", Bioconjugate Chem., 2008, 19, 1785-1795.
Mei, Bing C.; Eunkeu Oh; Kimihiro Susumu; Dorothy Farrell; T.J. Mountziaris and Hedi Mattoussi, "Effects of Ligand Coordination Number and Surface Curvature on the Stability of Gold Nanoparticles in Aqueous Solutions", Langmuir, 2009, 25, 10604-10611.
Mei, Bing C.; Kimihiro Susumu; Igor L. Medintz and Hedi Mattoussi, "Polyethylene glycol-based bidentate ligands to enhance quantum dot and gold nanoparticle stability in biological media", Nat. Protocols, 2009, 4, 412-423.
Mei, Bing C.; Kimihiro Susumu; Igor L. Medintz; James B. Delehanty; T. J. Mountziaris and Hedi Mattoussi, "Modular poly(ethylene glycol) ligands for biocompatible semiconductor and gold nanocrystals with extended pH and ionic stability", J. Mater. Chem., 2008, 18, 4949-4958.
Susumu, Kimihiro; H. Tetsuo Uyeda; Igor L. Medintz and Hedi Mattoussi, "Design of Biotin-Functionalized Luminescent Quantum Dots", J. Biomed. Biotech., 2007, Article ID 90651.
Susumu, Kimihiro; Bing C. Mei and Hedi Mattoussi, "Multifunctional ligands based on dihydrolipoic acid and polyethylene glycol to promote biocompatibility of quantum dots", Nat. Protocols, 2009, 4, 424•-436.
Susumu, Kimihiro; H. Tetsuo Uyeda; Igor L. Medintz; Thomas Pons; James B. Delehanty and Hedi Mattoussi, "Enhancing the Stability and Biological Functionalities of Quantum Dots via Compact Multifunctional Ligands", J. Am. Chem. Soc., 2007, 129, 13987-13996.
Uyeda, H.T., Medintz, I.L., Jaiswal, J.K., Simon, S.M., Mattoussi, H. Synthesis of compact multidentate ligands to prepare stable hydrophilic quantum dot fluorophores. J Am. Chem. Soc. 2005, 127, 3870-3878.
Stewart et al., J. Am. Chem. Soc. 2010, 132, 9804-9813.
Internation Search Report and Written Opinion in PCT/US2012/049106.
Susumu et al., Multifunctional Compact Zwitterionic Ligands for Preparing Robust Biocompatible Semiconductor Quantum Dots and Gold Nanoparticles. J. Am. Chem. Soc. 2011,133, pp. 9480-9496.

\* cited by examiner

Primary Examiner — Michael G Hartley
Assistant Examiner — Lance Rider
(74) Attorney, Agent, or Firm — Amy Ressing; Roy Roberts (57) ABSTRACT

A ligand design allows compact nanoparticle materials, such as quantum dots (QDs), with excellent colloidal stability over a wide range of pH and under high salt concentrations. Self-assembled biomolecular conjugates with QDs can be obtained which are stable in biological environments. Energy transfer with these ligands is maximized by minimizing distances between QDs/nanoparticles and donors/acceptors directly attached to the ligands or assembled on their surfaces.

12 Claims, 8 Drawing Sheets

COMPACT MULTIFUNCTIONAL LIGAND TO ENHANCE COLLOIDAL STABILITY OF NANOPARTICLES

BACKGROUND

Biocompatible nanoparticles (NPs), including quantum dots (QDs), exploit the unique size-dependent properties of their constituent materials and can serve various important roles in a biological context. For example, such nanoparticle materials have attracted significant interest in their use for cellular labeling and in vivo imaging studies. Various uses of nanoparticles are described in, e.g., Algar et al, Bioconjugate Chem. 2011, 22, 825-858 (2011); U.S. Pat. No. 7,858,386; and U.S. Patent Application Publication Nos. 2008/0087843, 2011/0089241, and 2011/0097797, each of which is incorporated herein by reference.

For use of semiconductor quantum dots (QDs) and gold nanoparticles (AuNPs) in biological applications, good pH and ionic stability as well as small hydrodynamic volume are desirable. These properties of NPs can depends on which "ligand" coats the surface of the NPs to provide aqueous stability to the NPs and facilitate their integration within biological systems. Various families of ligand molecules have been utilized for these purposes, with each usually providing its own set of functional benefits and liabilities. However, a need remains for compact multifunctional ligands for nanoparticles that provide a desired combination of features.

BRIEF SUMMARY

In a first embodiment, a composition comprises a compound selected from the group consisting of wherein (A) is either wherein each respective dashed line represents an amide bond, and wherein (B) and (C) are each independently selected from the group consisting of 2-hydroxyethyl, 3-carboxyl propyl, 2-carboxyethyl, 2-2-aminoethyl, and 2-sulfoethyl.

In another embodiment, a method of modifying a nanoparticle comprises contacting with a composition of the first embodiment.

In a further embodiment, a composition comprises a compound selected from the group consisting of wherein each instance of (A) is independently selected from the group consisting of wherein each respective dashed line represents an amide bond, and wherein each instance of (B) is independently selected from the group consisting of 2-hydroxyethyl, 3-carboxypropyl, 2-carboxyethyl, 2-2-aminoethyl, and 2-sulfoethyl.

BRIEF DESCRIPTION OF THE DRAWINGS

FIG. 1 shows chemical structures of various ligands.

FIG. 3 shows luminescence images for quantum dots (QDs) in phosphate buffered saline at various pH values. CdSe—ZnS QDs emitting at 550 nm were used and were excited with a hand-held UV lamp at 365 nm.

DETAILED DESCRIPTION

Definitions

Use of the singular forms "a," "an," and "the" include plural references unless the context clearly dictates otherwise. Thus, for example, reference to "a nanoparticle" includes a plurality of such nanoparticles.

The terms "semiconductor nanocrystal," "quantum dot," and "QD" are used interchangeably herein and refer to an inorganic crystallite of about 1 nm or more and about 1000 nm or less in diameter or any integer or fraction of an integer therebetween, preferably at least about 2 nm and about 50 nm or less in diameter or any integer or fraction of an integer therebetween, more preferably at least about 2 nm and about 20 nm or less in diameter (for example about 2, 3, 4, 5, 6, 7, 8, 9, 10, 11, 12, 13, 14, 15, 16, 17, 18, 19, or 20 nm). QDs are characterized by their relatively uniform nanometer size.

A QD is capable of emitting electromagnetic radiation upon excitation (the QD is luminescent) and includes a "core" of one or more first semiconductor materials, with the core optionally surrounded by a "shell" of a second semiconductor material.

The term "nanoparticle" or "NP" as used herein includes the above-mentioned QDs in addition to other nano-scale and smaller particles such as metallic nanoparticles (e.g., nanoparticles comprising Ag, Au, Cu, Pd, Pt, and combinations thereof), carbon nanotubes, proteins, polymers, dendrimers, viruses, and drugs. A nanoparticle has a size of less than about 1 micron, optionally less than about 900, 800, 700, 600, 500, 400, 300, 200, 100, 80, 60, 50, 40, 30, 20, 10, 9, 8, 7, 6, 5, 4, 3, 2, or 1 nanometers. A nanoparticle may have various shapes such as a rod, a tube, a sphere, and the like. Nanoparticles may be made from various materials including metals, carbon (such as carbon nanotubes), polymers, and combinations thereof.

Description

Coating of nanoparticles (NPs) with ligands preferably provides the NPs with a number of traits. The ligand coat should confer long-term colloidal stability across a wide pH and buffer range to myriad types of monodispersed NPs, while ideally exhibiting the following features: ease of synthesis in bulk quantities; a small size that minimizes the hydrodynamic radius of the subsequently functionalized NP; high-affinity attachment to the NP while still allowing other molecules access to the NP surface; an available "handle" for further chemical modification in a relatively simple manner; minimal undesired interactions with other molecules native to biological environments, e.g., opsonization; minimal to no toxicity and potentially allow for clearance of the NP conjugate after in vivo administration; and minimal perturbation of inherent NP properties (e.g., spectral properties). It has been challenging to design NP ligands that can provide a majority of these properties, let alone all, in a single molecule.

Ligands vary widely in structure. Beyond being utilized for direct NP synthesis, interactions of ligands with NPs can be loosely grouped into two functional mechanisms. In one mechanism, encapsulation with amphiphilic polymeric ligands or similar dendrimeric material interacts with and overcoat the native surface while simultaneously mediating colloidal stability. This approach, however, usually comes at the expense of a much larger hydrodynamic size which is normally undesirable. In contrast, cap exchange replaces the original hydrophobic surface ligands with bifunctional hydrophilic ligands via mass action to render the NPs water-soluble.

The bidentate-thiol dihydrolipoic acid (DHLA) has been used as a ligand. See FIG. 1C and Mattoussi et al., *J. Am. Chem. Soc.* (2000) 122:12142-12150. The bidentate-thiols essentially function as cooperative anchoring groups that strongly coordinate to the nanocrystal surface with the charged carboxyl group at the molecule's other end mediating colloidal stability. The compact size of DHLA ligands also allows direct self-assembly of a variety of materials onto a nanoparticle surface, such as oligohistidine-tagged (His-tagged) peptides, proteins and DNA. However, aqueous solubility of DHLA-coated QDs relies on deprotonation of the terminal carboxyl groups so that their colloidally-stable pH window is limited to basic pH. In contrast, amine-coated QDs are colloidally stable at moderate acidic pH, however, their stability drops when moving to neutral to basic conditions.

Other ligands achieve solubility through poly(ethylene glycol) (PEG) moieties (typically having molecular weight ranging from 400 to 1000, or greater) appended to a DHLA anchor group, thus providing QDs with a wider range of pH stability. See Uyeda et al., *J. Am. Chem. Soc.* (2005) 127: 3870-3878. However, the long chain length of the PEG unit was found to undesirably increase the QDs hydrodynamic size and sterically prohibit conjugation of His-tagged proteins directly onto the QD surface.

Thus, previously-described ligands for nanoparticles suffer from a number of disadvantages. They often provide only limited colloidal stability under narrow pH ranges. The PEG moieties produce an undesirably thick surface coating layer on NPs and hamper efficient energy transfer and direct conjugation onto NP surfaces, and furthermore are hard to synthesize, have large size/mass and are usually obtained as a polydisperse mixture.

Figure 1A:
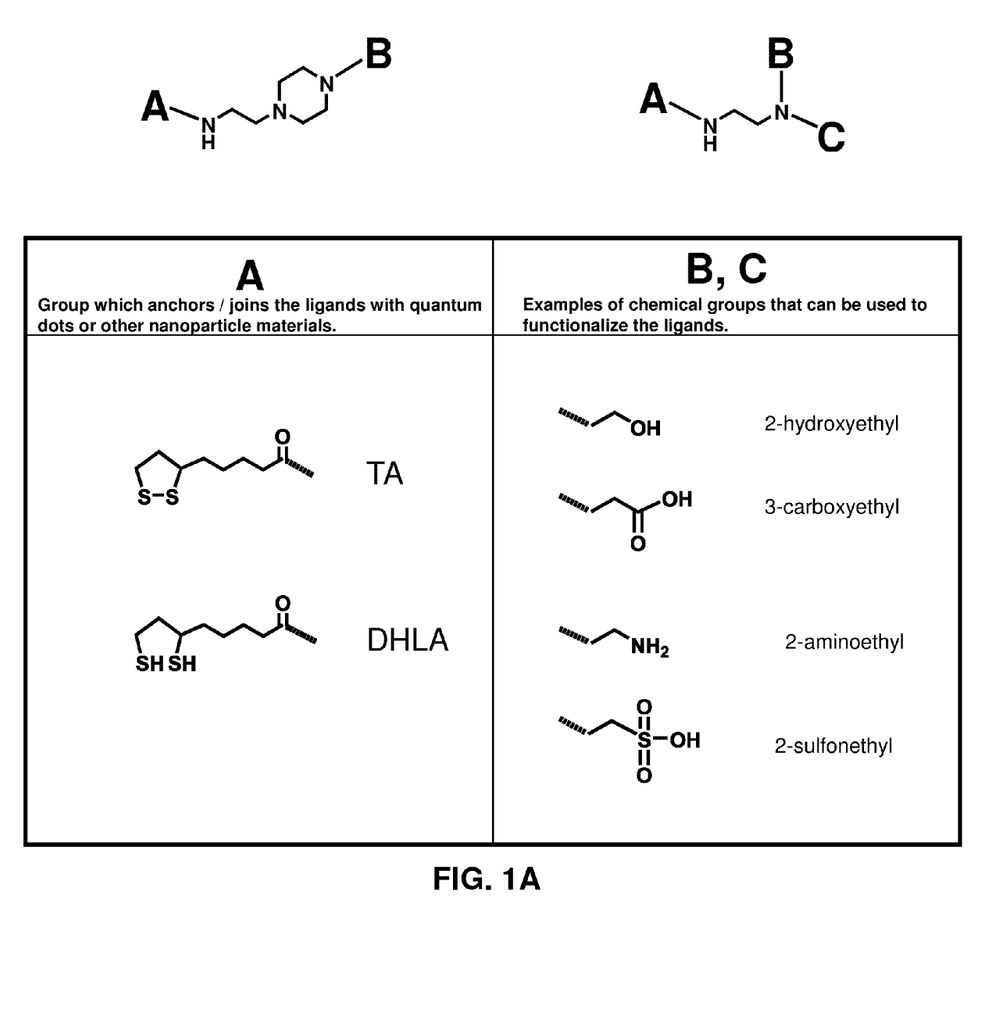
FIG. 1A illustrates chemical backbones for compact ligands (CLs) and various functional groups associated therewith. "TA" represents thioctic acid and "DHLA" represents dihydrolipoic acid.
Figure 1B:
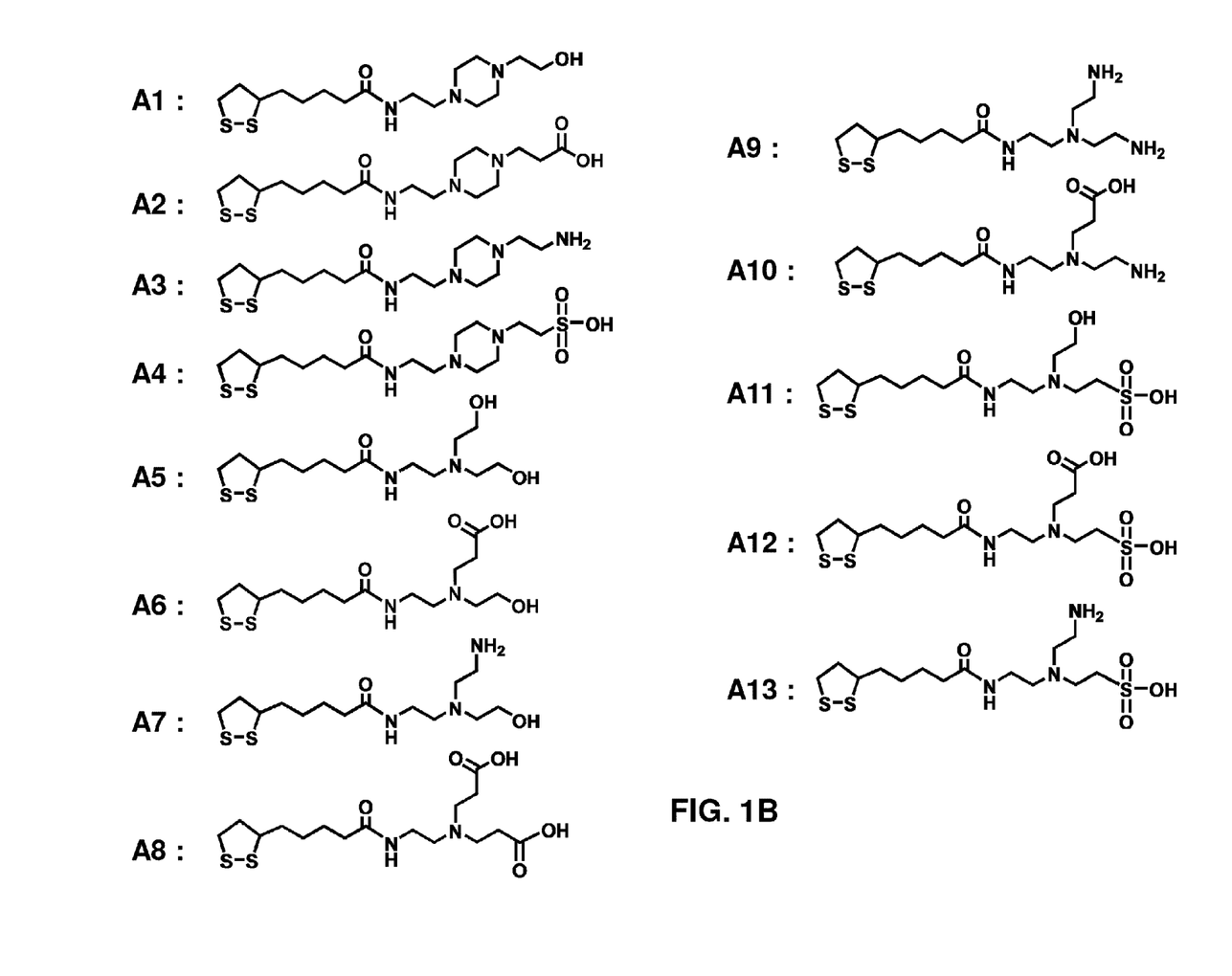
FIG. 1B illustrates thirteen exemplary compact ligands denoted A1 through A13. These ligands could also exist in the DHLA form.

Described herein are a new class of compact ligands which can provide nanoparticles with extended pH stability and salt stability without the undesired increase in apparent hydrodynamic size observed with PEG-based ligands. In contrast to utilizing a carboxyl or PEG moiety to mediate colloidal stability, this ligand design relies on an inherent zwitterionic nature. Exemplary chemical formulae for such compact ligands (CLs) are shown in FIG. 1.

Exemplary thioctic acid (TA)- and DHLA-based compact multifunctional ligands incorporate amino and carboxyl groups for aqueous solubility and biofunctionalization, thereby reducing the size of ligand-coated NPs without sacrificing stability. Protonation of amino group would maintain aqueous solubility of nanoparticles under acidic pHs while deprotonation of carboxyl group would do the same under basic pHs. Other polar functional groups such as hydroxy and sulfonate groups would also help aqueous solubility of NPs. Overall, a wide range of pH stability is expected by adopting those features for the new ligand designs. Either amino or carboxyl group would also be available for common bioconjugation chemistry. The molecular weight of the new ligands are normally less than half that of the previous DHLA-PEG series, resulting in an overall reduction in the NP size and the hydrodynamic volume. QD dispersions capped with the new ligands were found to be colloidally stable and remained fluorescent over the range from pH 4 to pH 12 for at least 2 months.

Preferably, a quantum dot with a hard diameter of about 4 nm (for example 4.0±0.29 nm) coated with the compact ligand has a hydrodynamic diameter of less than 10 nm, optionally less than 9 nm.

Characterization of QDs coated with the compact ligands (CL-QDs) included examining surface charge, wettability, hydrodynamic volumes, pH and salt stability, testing direct conjugation of His-tagged proteins and peptides, aqueous covalent-coupling chemistry, peptide-mediated cellular uptake and microinjection, cellular imaging, and cytotoxicity. The properties of this compact ligand series can be extended to AuNPs in a similar fashion.

Compact Ligand Design

Figure 5:
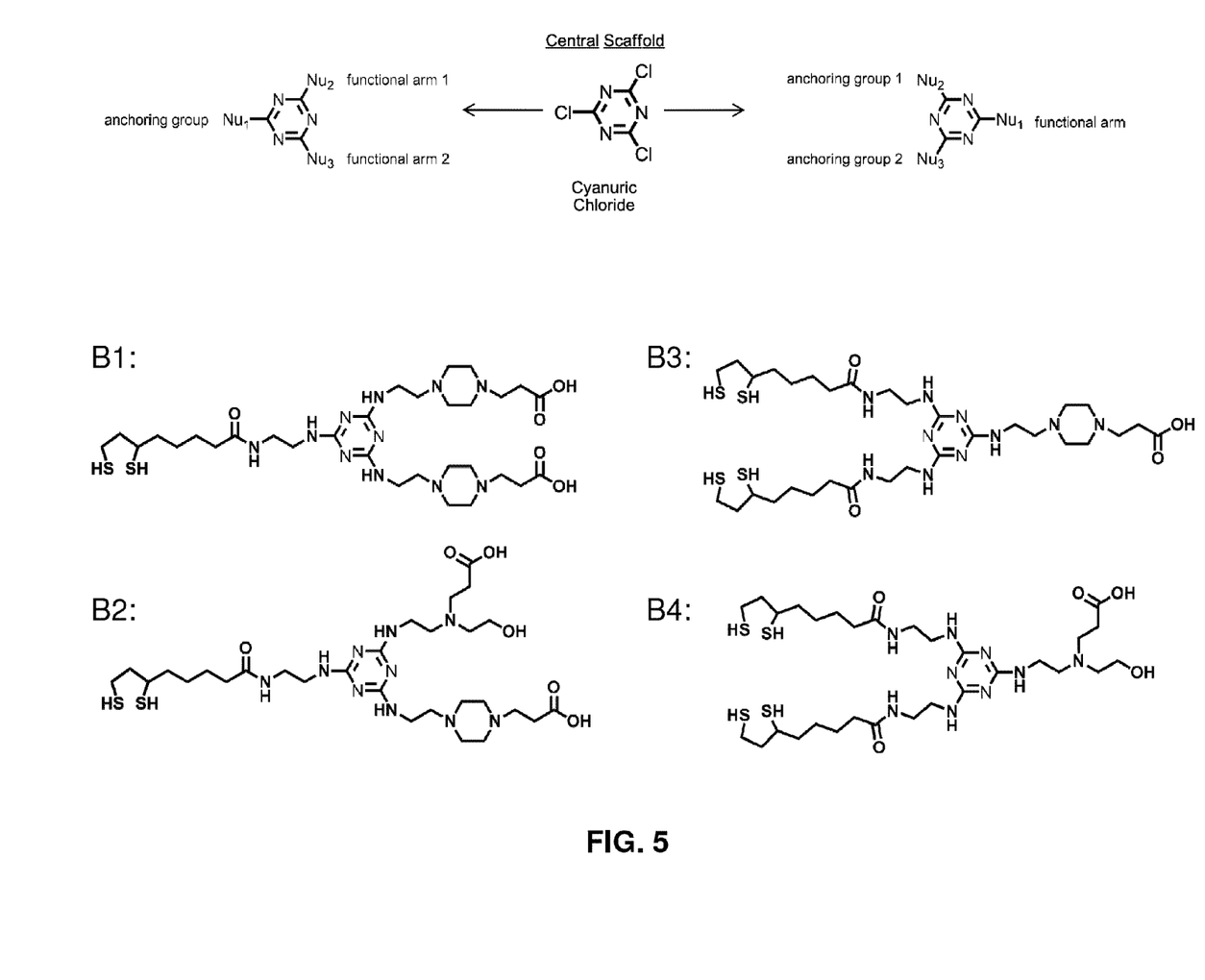
FIG. 5 illustrates embodiments of compact ligands comprising a central scaffold of 1,3,5-triazine.

The compact ligands described herein have discrete functional modules which provide various properties due to their chemical structures. Examples illustrating the modular nature of the compact ligands are shown in FIGS. 1A and 5. The compact ligands preferably have one or more anchoring modules and one or more functionalization modules, most preferably one or two of each type of module.

An anchoring module (also termed an anchoring group) serves to attach the compact ligand to the nanoparticle and may also help mediate solubility. Preferably, the anchoring module is either TA or DHLA, with attachment mediated by the dithiolane motif of TA and/or the bidentate dithiol motif of DHLA. The module provides a high-affinity attachment that, at least in the case of bidentate thiol, is superior to that of QDs coated with monothiol ligands in aqueous solutions.

The functionalization module (also termed a functional arm) is preferably selected from 2-hydroxyethyl, 3-carboxypropyl, 2-carboxyethyl, 2-2-aminoethyl, and 2-sulfoethyl. This module allows for chemical functionalization of the compact ligands and may also help mediate solubility.

Rather than depending upon PEG to mediate aqueous solubility in a second module, the compact ligands described herein can incorporate at least two functional groups including carboxyl and/or amine (frequently secondary or tertiary amine, but optionally primary amine) in order to maintain aqueous solubility in a wide pH range mainly via a zwitterionic character. These groups are preferably configured to serve multiple, simultaneous roles. Besides imparting aqueous solubility under basic pH, carboxyl groups can be used for further coupling chemistry with biological molecules or organic dyes; this provides a third module or utility to the ligands. A tertiary amino group is expected to enhance aqueous solubility under acidic pH and remain chemically inert to common bioconjugation chemistries such as carbodiimide coupling, such as 1-ethyl-3-(3-dimethylaminopropyl)carbodiimide (EDC). Use of tertiary amine also prevents EDC-based cross-linking (to carboxyls) between the surface ligands on QDs and negates potential issues of cellular toxicity previously noted in the presence of ligands displaying primary amines.

Figure 1C:
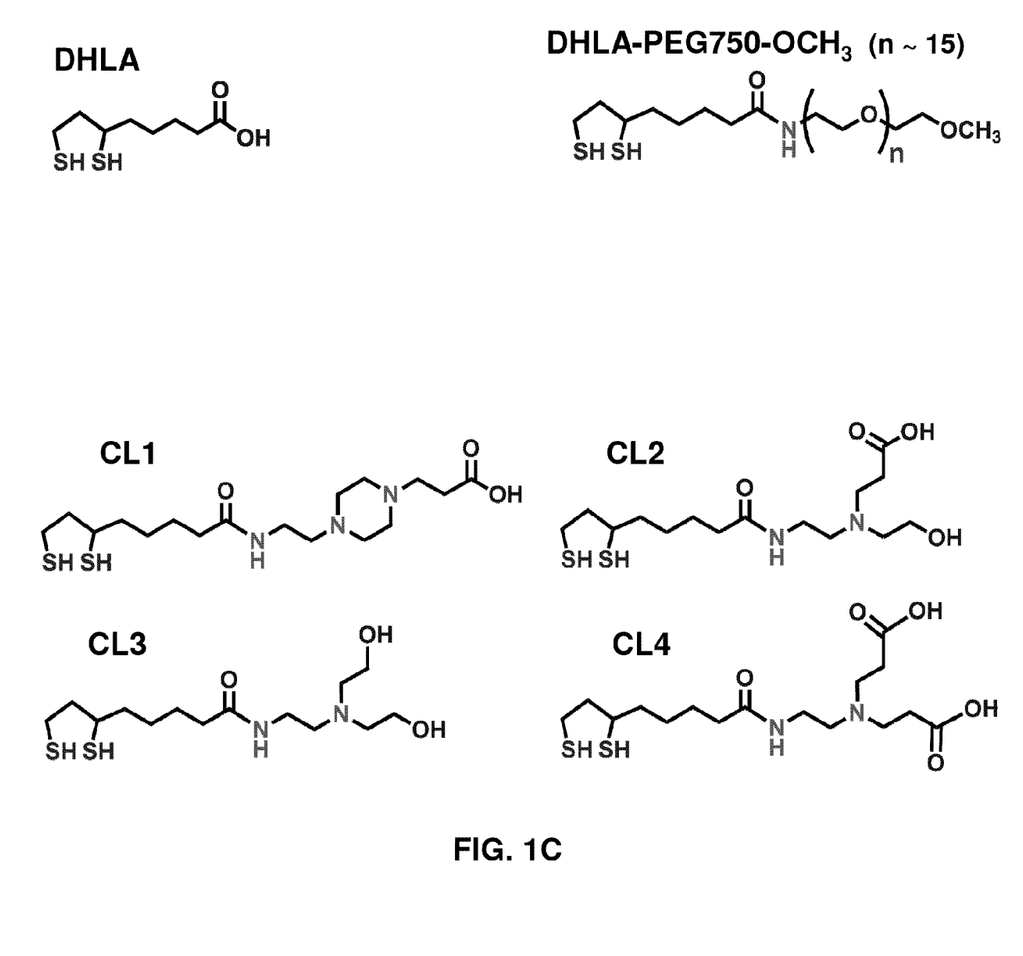
FIG. 1C illustrates additional ligands including non-compact ligands and exemplary compacts ligands CL1, CL2, CL3, and CL4.

The chemical structures of the exemplary compact ligands CL1 through CL4, as well as comparative ligands DHLA and DHLA-PEG750-OCH$_3$, are illustrated in FIG. 1C. CL1 incorporates two tertiary amines in a piperazine ring structure and terminates in an alkyl carboxyl group. CL2 includes a single tertiary amine that displays both an alkyl carboxyl and a hydroxyl group. CL3 is similar to CL2 but ends in two hydroxyl groups. This ligand essentially functions as (i) a control to ascertain any necessity for having both a carboxyl and a tertiary amine simultaneously present in the same ligand, and (ii) to verify if the carboxyl group(s) could be substituted with a hydroxyl function. DHLA which represents the non-amine control ligand. CL4 continues with the same CL2 and CL3 motif, but terminates in two alkyl carboxyl groups. The estimated pKa values of the key ionizable groups on each ligand are given in Table I below. CL1, CL2 and CL4 all display values in both the acidic and basic pH regime matching our key design criteria. In terms of size and mass, CL1-CL4 are estimated to be up to twice the ~1.0 nm extended length of DHLA and less than twice the mass, see Table I. This contrasts strongly with the DHLA-PEG750-OCH$_3$ sample (also seen in FIG. 1C), which has been used as a ligand and which has an estimated persistence length of up to 6.8 nm (~6-7 times longer than that of DHLA) along with a mass ~4.5 times larger than that of DHLA.

Compact Ligand Synthesis

Figure 2A:
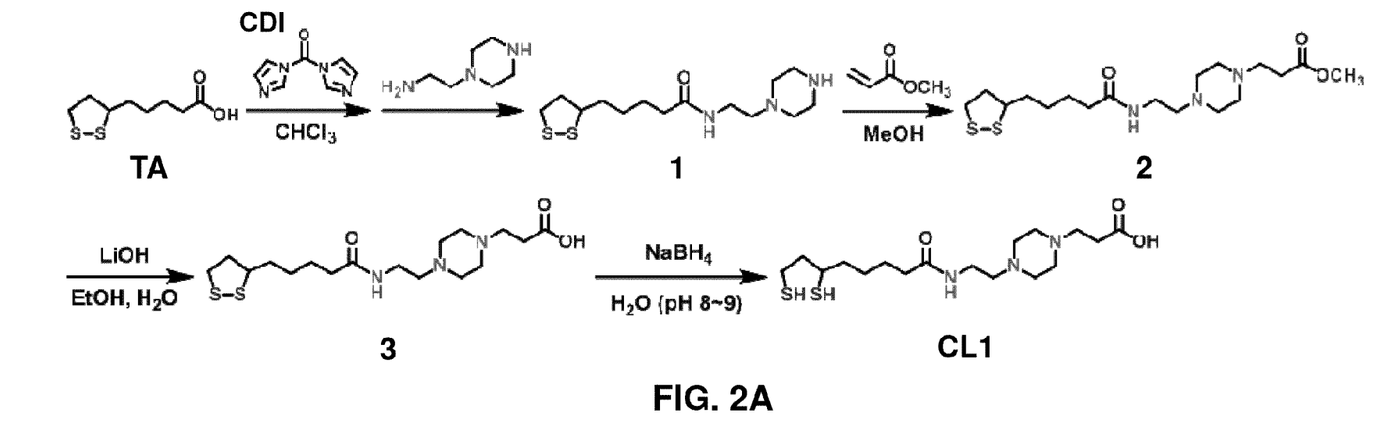
FIGS. 2A, 2B, 2C, and 2D show synthetic schemes for preparing exemplary compacts ligands CL1, CL2, CL3, and CL4, respectively.
Figure 2B:
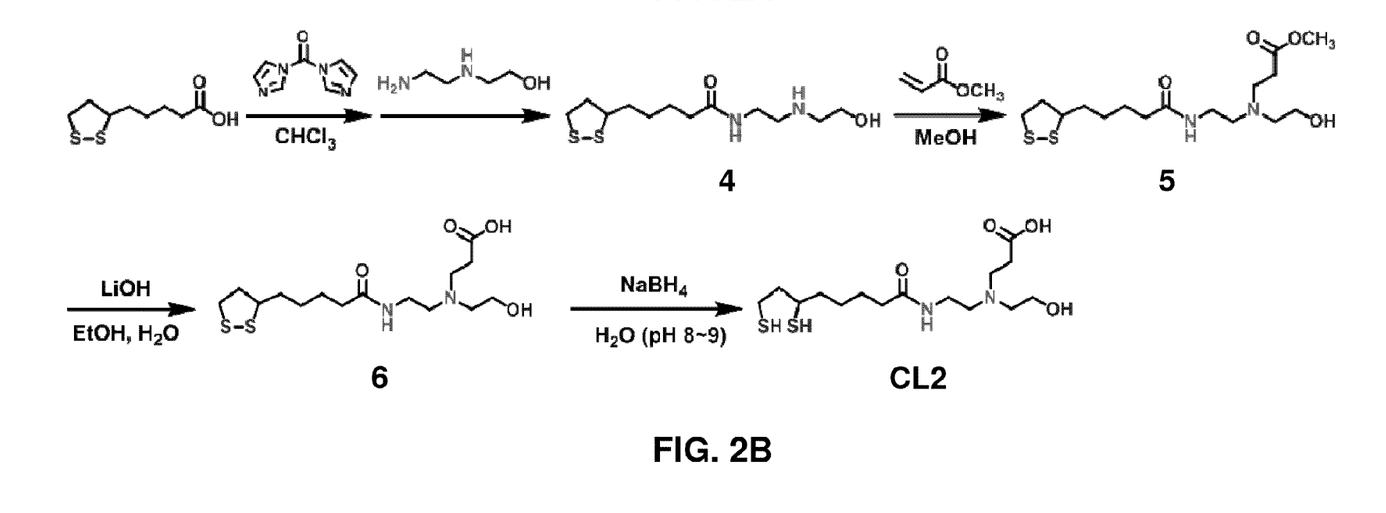
Figures 2C, 2D:
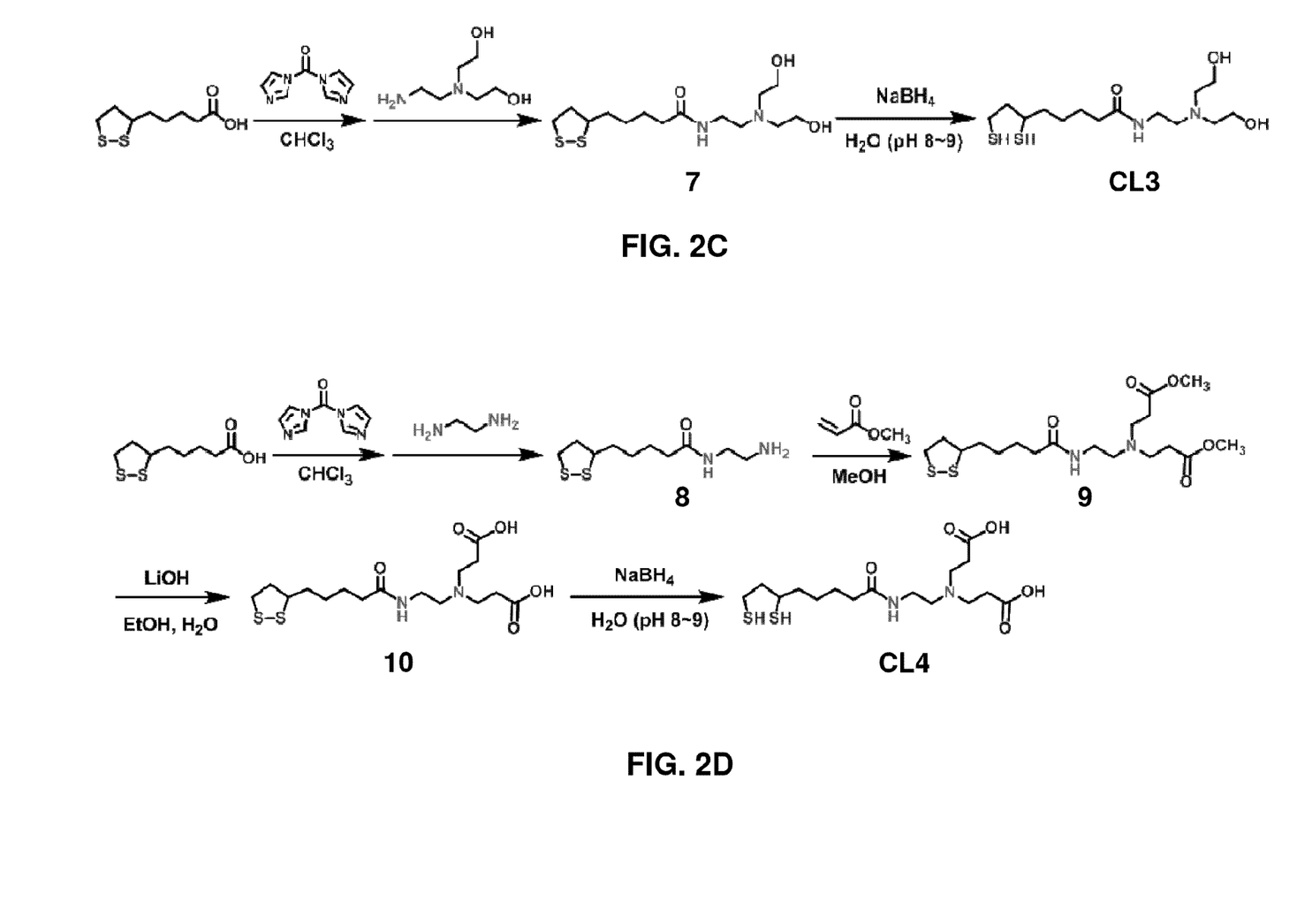

The exemplary compact ligands CL1, CL2, CL3, and CL4 were prepared as described below and illustrated in FIGS. 2B and 2C, using the described intermediate numbered compounds. Other compact ligands may be synthesized by one of ordinary skill in the art using variations of the described techniques.

The reaction conditions were optimized and the number of reaction steps minimized. This is an important issue since subsequent QD cap exchange is a mass-driven reaction and thus requires a large excess of ligand per QD to ensure full overcoating. Synthesis of the CL1 through CL4 compact ligands starts from modification of the carboxyl group of thioctic acid (TA) with a primary amine compound. Use of 1,1'-carbonyldiimidazole (CDI) as a coupling reagent is key to the chemistry utilized here as it exclusively gives you a primary amine-coupled product in high yield in the presence of a secondary amine group (1 and 4). This reaction step significantly simplifies the entire synthetic process by avoiding the need for protecting groups. Subsequent Michael addition reactions of 1, 4, and 8 with methyl acrylate formed 2, 5 and 9, respectively. The last steps of the ligand synthetic procedures are (i) deprotection of the methyl ester group to yield the carboxyl group (2 to 3, 5 to 6, and 9 to 10) and (ii) the ring opening reduction from a disulfide group to a dithiol group (3 to CL1, 6 to CL2, 7 to CL3 and 10 to CL4). Since both of these reactions are simple and quantitative, and each product is highly soluble in water, the reactions were successively performed in aqueous solution. Each ligand required four synthetic preparatory steps except CL3 which only necessitated two steps. This includes the ring opening step which is necessary when cap exchanging QDs with all DHLA-based ligands. Each synthetic step for CL1-CL4 was straightforward and had a reasonably high yield, clearly fulfilling the desired criteria of facile synthesis of large quantities (gram scale). Final CL products were used directly for the cap exchange reaction with QDs coated with the native synthetic hydrophobic ligands. All the compounds (2, 5, 7, 9) utilized for the subsequent cap exchange were found to be stable for at least 6 months to a year when stored in a refrigerator.

Given the high reaction yield of the ligands and their presence in aqueous solution, we opted to utilize a biphasic mixture for cap exchange rather than the single phase method used previously. The cap exchange reaction was initiated by injecting the hydrophobic QDs dissolved in CHCl$_3$ into the aqueous ligand solution under a N$_2$ atmosphere with vigorous stirring. As the reaction proceeds, the QDs were gradually transferred from the CHCl$_3$ layer to the aqueous layer in a few hours. The reaction mixture was left with vigorous stirring overnight. Purified QDs were found to be well dispersed in water and colloidally stable over months without any sign of aggregation.

Compounds 1 and 2. Thioctic acid (3.00 g, 1.45×10$^{-2}$ mol) and 1,1'-carbonyldiimidazole (2.59 g, 1.60×10$^{-2}$ mol) were added to a 100-ml round-bottom flask, and the mixture was purged with N$_2$. 30 ml of toluene was added to the mixture by syringe, and the reaction mixture stirred at room temperature for 1 h under N$_2$. The mixture was transferred to an addition funnel and CHCl$_3$ (20 ml) was further mixed in, and then this was added dropwise over 30 min to a mixture of N-(2-2-aminoethyl)piperazine (2.10 ml, 1.59×10$^{-2}$ mol) and 30 ml of CHCl$_3$ in a 250-ml two-neck round-bottom flask cooled in an ice-bath under N$_2$. The reaction mixture was further stirred at room temperature overnight and transferred to a separatory funnel. CHCl$_3$ (~100 ml) and deionized water (~100 ml) were added to the mixture and the CHCl$_3$ layer was collected. The aqueous layer was further washed with CHCl$_3$ (2 times). The combined organic layers were dried over Na$_2$SO$_4$, filtered, and concentrated to ~20 ml by rotary evaporator. The crude product solution was chromatographed on silica gel with CHCl$_3$:MeOH (5:1) as the eluent. The product fractions were concentrated to ~10 ml and directly used for the next reaction.

Product solution was dissolved in 80 ml of MeOH and purged with N$_2$. Methyl acrylate (5.0 ml, 5.6×10$^{-2}$ mol) was added dropwise and the reaction mixture stirred at room temperature overnight under N$_2$. The solvent and excess methyl acrylate was subsequently evaporated, and the residue was chromatographed on silica gel with CHCl$_3$:MeOH (20:1) as the eluent. Yield=3.448 g (59% in 2 steps based on 3.00 g of thioctic acid). N-[2-(1-piperazinyl)ethyl]-5-(1,2-dithiolan-3-yl)pentanamide (1): $^1$H NMR (400 MHz, CDCl$_3$): δ 6.05 (br s, 1H, NH), 3.52-3.63 (m, 1H), 3.35 (q, 2H, J=7.6 Hz, —CH$_2$—), 3.07-3.23 (m, 2H), 2.89 (t, 4H, J=6.4 Hz, —CH$_2$—), 2.37-2.53 (m, 7H), 2.20 (t, 2H, J=10.0 Hz, —CH$_2$—CO—), 1.86-1.97 (m, 1H), 1.55-1.8 (m, 4H), 1.4-1.55 (m, 2H). ESI MS m/z: 318.1743 (M+H)$^+$/calculated 318.167. N-{2-[4-(methoxycarbonylethyl)piperazin-1-yl]ethyl}-5-(1,2-dithiolan-3-yl)pentanamide (2): $^1$H NMR (400 MHz, CDl$_3$): δ 6.08 (br s, 1H, NH), 3.69 (s, 3H, —OCH$_3$), 3.52-3.63 (m, 1H), 3.34 (q, 2H, J=7.6 Hz, —CH$_2$—), 3.07-3.23 (m, 2H), 2.71 (t, 2H, J=9.6 Hz, —CH$_2$—), 2.40-2.58 (m, 13H, —CH$_2$—), 2.20 (t, 2H, J=9.8 Hz, —CH$_2$—CO—), 1.86-1.97 (m, 1H), 1.6-1.8 (m, 4H), 1.4-1.55 (m, 2H). ESI MS m/z: 404.2018 (M+H)$^+$/calculated 404.204.

Compounds 4 and 5. Thioctic acid (4.00 g, 1.94×10$^{-2}$ mol) and 1,1'-carbonyldiimidazole (3.46 g, 2.13×10$^{-2}$ mol) were added to a 100-ml round-bottom flask, and the mixture was purged with N$_2$. 50 ml of CHCl$_3$ was added to the mixture by syringe and the reaction mixture stirred at room temperature overnight under N$_2$ and then transferred to an addition funnel where CHCl$_3$ (20 ml) was further mixed in, and the resulting solution was added dropwise over 30 min to a mixture of N-(2-hydroxyethyl)ethylenediamine (2.20 ml, 2.18×10$^{-2}$ mol) and 40 ml of CHCl$_3$ in a 250-ml two-neck round-bottom flask cooled in an ice-bath under N$_2$. The reaction mixture was further stirred at room temperature for 5 h and transferred to a separatory funnel. Saturated sodium bicarbonate solution (~100 ml) was added to the mixture and the CHCl$_3$ layer was collected. The aqueous layer was further washed with CHCl$_3$ (4 times). The combined organic layers were dried over Na$_2$SO$_4$, filtered, and concentrated to ~20 ml by rotary evaporator. The crude product solution was chromatographed on silica gel with CHCl$_3$:MeOH (5:1) as the eluent. The product fractions were concentrated to ~10 ml and used for the next reaction. Product solution was dissolved in 80 ml of MeOH and purged with N$_2$. Methyl acrylate (9.0 ml, 0.10 mol) was added dropwise and the reaction mixture was stirred at room temperature overnight under N$_2$. The solvent and excess methyl acrylate was evaporated. The residue was chromatographed on silica gel with CHCl$_3$:MeOH (10:1) as the eluent. Yield=3.584 g (49% in 2 steps based on 4.00 g of thioctic acid). N-{2-[(2-hydroxyethyl)amino]ethyl}-5-(1,2-dithiolan-3-yl)pentanamide (4): $^1$H NMR (400 MHz, CDCl$_3$): δ 5.97 (br s, 1H, NH), 3.68 (t, 2H, J=6.8 Hz, —CH$_2$—), 3.53-3.62 (m, 1H), 3.37 (q, 2H, J=7.6 Hz, —CH$_2$—), 3.07-3.23 (m, 2H), 2.79 (t, 2H, J=6.8 Hz, —CH$_2$—), 2.78 (t, 2H, J=7.8 Hz, —CH$_2$—), 2.41-2.52 (m, 1H), 2.20 (t, 2H, J=9.8 Hz, —CH$_2$—CO—), 1.86-1.97 (m, 1H), 1.55-1.8 (m, 4H), 1.4-1.55 (m, 2H). ESI MS m/z: 293.1206 (M+H)$^+$/calculated 293.136. N-{2-[N'-(2-hydroxyethyl)-N'-(methoxycarbonylethyl)amino]ethyl}-5-(1,2-dithiolan-3-yl)pentanamide (5): $^1$H NMR (400 MHz, CDCl$_3$): δ 6.39 (br s, 1H, NH), 3.72 (s, 3H, —OCH$_3$), 3.52-3.63 (m, 3H), 3.33 (q, 2H, J=7.6 Hz, —CH$_2$—), 3.07-3.23 (m, 2H), 2.80 (q, 2H, J=8.2 Hz, —CH$_2$—), 2.60 (q, 4H, J=6.8 Hz, —CH$_2$—), 2.49 (t, 2H, J=8.0 Hz, —CH$_2$—), 2.41-2.53 (m, 1H), 2.21 (t, 2H, J=10.0 Hz, —CH$_2$—CO—), 1.86-1.97 (m, 1H), 1.6-1.8 (m, 4H), 1.4-1.55 (m, 2H). ESI MS m/z: 379.1720 (M+H)$^+$/calculated 379.173.

Compound 7. Thioctic acid (2.00 g, 9.69×10$^{-3}$ mol) and 1,1'-carbonyldiimidazole (1.73 g, 1.07×10$^{-2}$ mol) were added to a 100-ml round-bottom flask, and the mixture was purged with N$_2$. 20 ml of CHCl$_3$ was added to the mixture by syringe and the reaction mixture stirred at room temperature for 1 h under N$_2$. The mixture above was transferred to an addition funnel and CHCl$_3$ (5.0 ml) was further mixed in, and the resulting solution added dropwise over 30 min to a mixture of N,N-bis(2-hydroxyethyl)ethylenediamine (1.60 g, 1.08×10$^{-2}$ mol) and 20 ml of CHCl$_3$ in a 250-ml two-neck round-bottom flask under N$_2$. The reaction mixture was further stirred at room temperature overnight and poured into water (~100 ml). The CHCl$_3$ layer was collected and the product was further extracted with CHCl$_3$ (2 times). The combined organic layers were dried over Na$_2$SO$_4$ and filtered. The solvent was evaporated and the crude product was chromatographed on silica gel with CHCl$_3$:MeOH (20:1) as the eluent. Yield=2.614 g (80% based on 2.00 g of thioctic acid). N-{2-[N',N'-bis(2-hydroxyethyl)amino]ethyl}-5-(1,2-dithiolan-3-yl)pentanamide (7): $^1$H NMR (400 MHz, CDCl$_3$): δ 6.36 (br s, 1H, NH), 3.63 (t, 4H, J=6.8 Hz, —CH$_2$—), 3.53-3.62 (m, 1H), 3.36 (q, 2H, J =7.6 Hz, —CH$_2$—), 3.07-3.23 (m, 2H), 2.63-2.73 (m, 6H, —CH$_2$—), 2.41-2.52 (m, 1H), 2.21 (t, 2H, J=10.0 Hz, —CH$_2$—CO—), 1.86-1.97 (m, 1H), 1.55-1.8 (m, 4H), 1.4-1.55 (m, 2H). ESI MS m/z: 337.1788 (M+H)$^+$/calculated 337.162.

Compounds 8 and 9. Thioctic acid (3.00 g, 1.45×10$^{-2}$ mol) and 1,1'-carbonyldiimidazole (2.59 g, 1.60×10$^{-2}$ mol) were added to a 100-ml round-bottom flask and the mixture purged with N$_2$. 30 ml of CHCl$_3$ was added to the mixture by syringe and the reaction mixture stirred at room temperature for 1 h under N$_2$ and the solution transferred to an addition funnel and added dropwise over 1 h to a mixture of ethylenediamine (8.0 ml, 0.12 mol) and 30 ml of CHCl$_3$ in a 250-ml two-neck round-bottom flask at room temperature under N$_2$. The reaction mixture was further stirred at room temperature overnight and transferred to a separatory funnel. Deionized water (~100 ml) was added to the mixture and the CHCl$_3$ layer was collected. The aqueous layer was further washed with CHCl$_3$ (3 times). The combined organic layers were concentrated to ~20 ml and the crude product solution was chromatographed on silica gel with CHCl$_3$:MeOH (5:1) as the eluent. The product fractions were concentrated to ~15 ml and used for the next reaction step.

Product solution was dissolved in 70 ml of MeOH and purged with N$_2$. Methyl acrylate (10.0 ml, 0.11 mol) was added dropwise and the reaction mixture was stirred at room temperature for 2 days under N$_2$. The solvent and excess methyl acrylate was evaporated. The residue was chromatographed on silica gel with CHCl$_3$:MeOH (20:1) as the eluent. Yield=3.919 g (64% in 2 steps based on 3.00 g of thioctic acid). N-(2-2-aminoethyl)-5-(1,2-dithiolan-3-yl)pentanamide (8): $^1$H NMR (400 MHz, CDCl$_3$): δ 6.06 (br s, 1H, NH), 3.53-3.62 (m, 1H), 3.31 (q, 2H, J=7.7 Hz, —CH$_2$—), 3.07-3.26 (m, 2H), 2.84 (t, 2H, J=7.8 Hz, —CH$_2$—), 2.41-2.52 (m, 1H), 2.21 (t, 2H, J=10.0 Hz, —CH$_2$—CO—), 1.86-1.97 (m, 1H), 1.6-1.8 (m, 4H), 1.4-1.6 (m, 2H). ESI MS m/z: 249.0941 (M+H)$^+$/calculated 249.110. N-{2-[N'N'-bis(methoxycarbonylethyl)amino]ethyl}-5-(1,2-dithiolan-3-yl)pentanamide (9): $^1$H NMR (400 MHz, CDCl$_3$): δ 6.52 (br s, 1H, NH), 3.69 (s, 6H, —OCH$_3$), 3.53-3.63 (m, 1H), 3.33 (q, 2H, J=7.2 Hz, —CH$_2$—), 3.07-3.22 (m, 2H), 2.74 (t, 4H, J=8.6 Hz, —CH$_2$—), 2.53 (t, 2H, J=7.2 Hz, —CH$_2$—), 2.47 (m, 1H), 2.43 (t, 4H, J=8.6 Hz, —CH$_2$—), 2.22 (t, 2H, J=9.8 Hz, —CH$_2$—CO—), 1.85-1.97 (m, 1H), 1.6-1.8 (m, 4H), 1.4-1.6 (m, 2H). ESI MS m/z: 421.1647 (M+H)$^+$/calculated 421.183.

Ester Hydrolysis, Ring Opening and Cap Exchange of Compact Ligands onto Quantum Dots Typical procedures for preparing a ligand for cap exchange are as follows. LiOH (20.9 mg, 1.36×10$^{-8}$ mol) was added to a mixture of 2 (0.307 g, 7.61×10$^{-4}$ mol), EtOH (2.0 ml), deionized (DI) H$_2$O (1.0 ml). The reaction mixture was stirred at room temperature for 2 h. Completion of the ester hydrolysis was checked by TLC (thin layer chromatography) with CHCl$_3$:MeOH (5:1) as the eluent. For reducing the dithiolane group, 4M HCl was then added dropwise to the reaction mixture to adjust the pH to ~8 and NaBH$_4$ (60.6 mg, 1.60×10$^{-3}$ mol) was added to the aqueous solution, which was further stirred at room temperature for 1.5 h under N$_2$. 4M HCl was then added dropwise to the reaction mixture to adjust the pH to 7~8. The EtOH was evaporated, and the remaining aqueous solution was filtered through a cotton plug to remove precipitated salts. The filtered aqueous solution was sealed in a glass vial with a septum and purged with N$_2$. Cap exchange utilized a biphasic mixture reaction. QDs capped with native hydrophobic ligands (~7.7 nmol in 1.0 ml of CHCl$_3$) were injected by syringe into the aqueous ligand solution with vigorous stirring. The biphasic mixture was stirred at room temperature (or at ~50° C.) overnight under N$_2$. The CHCl$_3$ layer was discarded by syringe and the residual CHCl$_3$ in the aqueous layer was removed by evaporation. The aqueous layer was then filtered through a Millex-LCR membrane filter (pore size 0.45 µm, Millipore) and transferred to a centrifugal spin dialyzer (Amicon Ultra 50K, Millipore). The mixture was diluted with DI water and centrifuged at 3,400 rpm for 5~10 min and the clear, filtered solution was discarded. To remove excess unbound ligands and other byproducts, the QD dispersion was subject to a few additional rounds of centrifugation with DI water.

Cap Exchange of Compact Ligands onto Gold Nanoparticles

For cap exchange with AuNPs, the ligands prepared by ester hydrolysis step were used without subsequent ring opening reaction of the dithiolane groups due to the much stronger intrinsic Au-S interaction. Typical procedures for preparing a ligand for cap exchange and the following cap exchange are as follows. LiOH (3.4 mg, 1.4×10$^{-4}$ mol) was added to a mixture of 2 (38.0 mg, 9.42×10$^{-5}$ mol) and DI H$_2$O (1.0 ml). The reaction mixture was stirred at room temperature for 2 h. Completion of the ester hydrolysis was checked by TLC with CHCl$_3$:MeOH (5:1) as the eluent. 4M HCl was then added dropwise to the reaction mixture to adjust the pH to ~8. Citrate-stabilized AuNPs (5.8 nm diameter, 3.5 ml, 2.8×10$^{-10}$ mol) were added to the ligand solution (in case of ligand 7, 0.1 M NaOH was further added to adjust the pH of the reaction mixture to ~9), and the reaction mixture was stirred at room temperature overnight. The aqueous solution was filtered through a Millex-LCR membrane filter (pore size 0.45 µm, Millipore) and transferred to a centrifugal spin dialyzer (Amicon Ultra 50K, Millipore). The mixture was diluted with DI water and centrifuged at 3,200 rpm for 5~10 min and the clear, filtered solution was discarded. To remove excess unbound ligands and other byproducts, the AuNP dispersion was subject to a few additional rounds of centrifugation with DI water.

Compact Ligand Properties

Effect on QD Spectra

Absorption and photoluminescence (PL) spectra were measured for QDs capped with the native hydrophobic ligands in hexane prior to cap-exchange and compared to those functionalized with the CLs in H$_2$O. The absorption spectra measured before and after cap exchange were essentially unchanged, and occasionally showed only a few nm shift of the lowest absorption maxima from batch to batch; PL spectra also showed similar trends.

Wettability

Some insight into ligand dissolution and interactions with aqueous environments was provided by probing the relative wettability of each ligand. This was accomplished by drying uniform concentrations and volumes of each ligand-coated QD sample onto flat mica surfaces and measuring the subsequent contact angles of water drops using sessile drop goniometry. As listed in Table 1, DHLA surfaces produced the smallest contact angle at 5°, while PEGylated QD surfaces produce the largest with a value of 20°. The smaller the observed contact angle the better the relative interaction of water with a given surface coating. Data for the CL series are 10°, 8°, 6°, and 13° for CL1-4 QD surfaces, respectively. The smallest contact angle obtained for DHLA-QD and this could be partially attributed to its presence in basic buffer which was necessary to maintain their colloidal stability; electrolytes would enhance the hydrophilicity of the sample. All the other samples were in DI water. The contact angles of all the CL-QDs were smaller than that of the PEG-coated QDs where ethylene oxide repeat units are required for aqueous stability. This result suggests that introduction of multiple ionizable groups onto the surface ligands may enhance the hydrophilicity of QD surface and help aqueous solubility.

Hydrodynamic Size

The hydrodynamic diameters for the new compact ligands were investigated with dynamic light scattering (DLS) analysis. As shown in Table 1, the hydrodynamic diameters of the 550 nm emitting QDs coated with CL1-CL4 ranged from 8.6 to 9.8 nm. These values are comparable to the 10.8 nm measured for the same materials coated with DHLA and are much smaller than those functionalized with DHLA-PEG750-OMe (11.5 nm). The hard diameter of the CdSe—ZnS core-shell QD sample used in this analysis was directly measured by TEM to be 4.0±0.29 nm. The differences in sizes between hydrodynamic diameter and the hard core-shell size measured in all samples arise from the ligand layer's hydrodynamic interactions on the QD surface. The contribution of the CLs to the overall hydrodynamic radius is in the ~2.3-3.4 nm range, which is reasonably close to that estimated for the fully extended length of each CL (1.6~2 nm), see Table 1. The hydrodynamic volume of a colloidal NP is far more complex than this simple extrapolation and is controlled by not only the size and chemical nature of the surface coating materials but also by the size of the NP itself. Thus, the new CLs provide the functionalized QDs with hydrodynamic volumes comparable to or even smaller than that of DHLA, which is one of the smallest ligands currently utilized. Moreover, the hydrodynamic size is significantly smaller than that encountered when utilizing far longer PEGylated- or far larger polymer/dendrimer/block copolymer ligands to mediate QD solubility.

Stability

The long-term colloidal stability of the CL-QD complexes was evaluated across a wide pH range. QD dispersions were colloidally stable in weakly acidic to strongly basic pH conditions (pH 4~5 to 12~13) without apparent fluorescence quenching for at least a 2 month period. These same CL-QDs were also stable in DI water for at least 6 months. This excellent pH stability directly contrasts with that observed for DHLA-coated QDs. While colloidally stable in basic media, DHLA-coated QDs became unstable even in weakly acidic media in a few days.

FIG. 3 shows luminescence images for quantum dots (QDs) in phosphate buffered saline at various pH values.

Figure 3A:
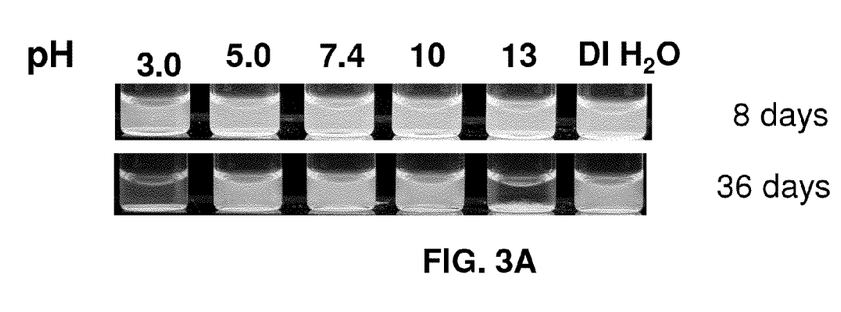
FIG. 3A shows QDs surface functionalized with DHLA-PEG-OMe at pH 3-13.
Figure 3B:
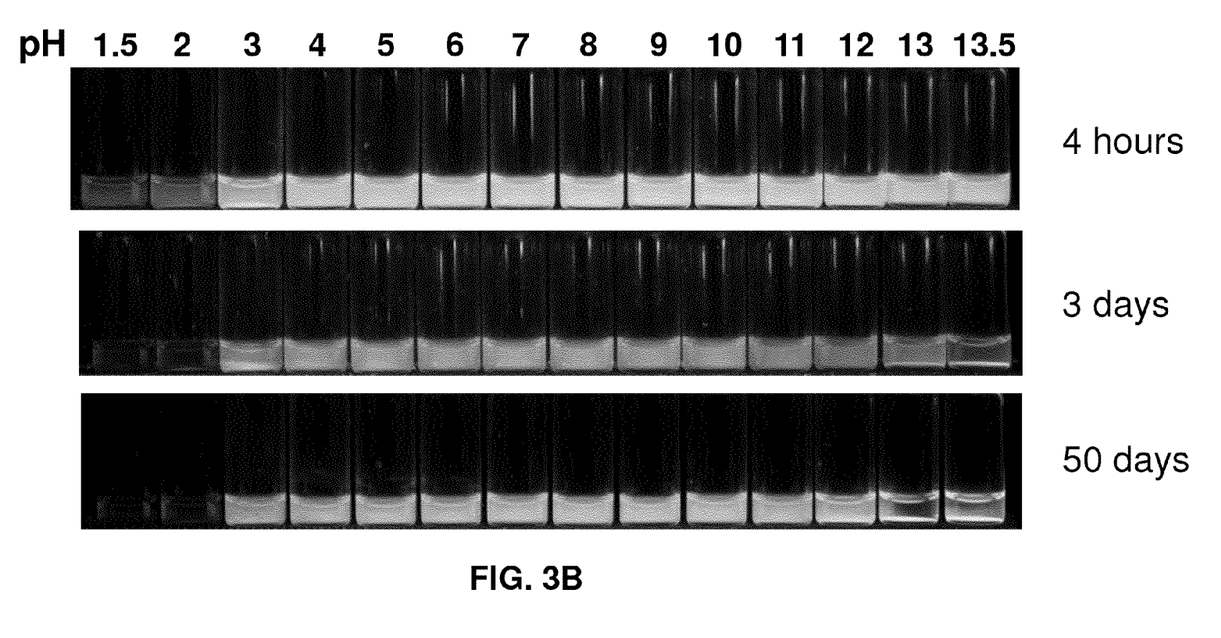
FIG. 3B shows QDs functionalized with the compact ligand CL2 (the DHLA form of A6) at pH 1.5-13.5

CdSe—ZnS QDs emitting at 550 nm were used and were excited with a hand-held UV lamp at 365 nm. FIG. 3A shows QDs with DHLA-PEG-OMe at pH 3-13. FIG. 3B shows QDs with the compact ligand CL2 at pH 1.5-13.5. It was found that QDs are colloidally stable at pH 4~13 for at least 2 weeks with new compact ligands. It is believed that the colloidal stability, among other aspects, reflects that the described compact ligands have a zwitterionic character through a wide range of pH values, generally from about pH 4 to 13 depending on the functional groups.

The capability of direct $His_n$-tagged protein conjugation onto CL-QD surfaces was examined in two ways: agarose gel electrophoretic separation and FRET analysis. As a test protein, the *E. coli* periplasmic MBP was used. This medium-sized protein (~44 kD) has dimensions of 30×40×65 Å with a volume of ~78×10³ Å³ and has found utility as a test platform in biosensing. MBP displaying a C-terminal pentahistidine sequence was site-specifically labeled on residue 95C with Texas Red maleimide dye (5×His MBP-TR). For gel electrophoretic analysis, dye-labeled MBP alone was self-as-

TABLE 1

Selected ligand or quantum dot functional and physical properties.

| | DHLA | CL1 | CL2 | CL3 | CL4 | DHLA-PEG750-OCH₃ |
|---|---|---|---|---|---|---|
| Molecular weight | 208.34 | 391.60 | 366.55 | 338.54 | 394.56 | 926.24 (n = 15) |
| Synthetic steps | 1 | 4 | 4 | 2 | 4 | 5 |
| Extended length[a] | ~1.0 nm | ~2.0 nm | ~1.8 nm | ~1.6 nm | ~1.8 nm | ~6.8 nm |
| $pK_a$[b] | 4.74 (carboxyl) | 2.87 (amine) | 3.59 (carboxyl) | 7.85 (amine) | 3.29 (carboxyl) | — |
| Dithiols (10.8/10.2) | | 4.55 (carboxyl) | 8.58 (amine) | 14.37 (OH) | 3.93 (carboxyl) | |
| Central amide (16.3) | | 7.58 (amine) | | 14.96 (OH) | 9.06 (amine) | |
| Chemical handle | Yes | Yes | Yes | No | Yes | No |
| Assembles $(His)_n$ peptide/protein | +/+ | +/+ | +/+ | +/+ | +/+ | +/− |
| Contact angles[c] | 5° | 10° | 8° | 6° | 13° | 20° |
| pH stability range over 4 weeks | 7-13 (4 days) | 4~5-13 | 4-13 | 4-13 | 5-13 | 4-11 |
| Zeta potential (mV)[d] | −20.3 ± 3.9 | −39.0 ± 1.9 | −19.8 ± 1.6 | −4.9 ± 0.8 | −50.8 ± 2.7 | — |
| DLS (% Intensity)[e] | 10.8 ± 2.70 | 8.6 ± 1.76 | 9.3 ± 1.66 | 9.5 ± 2.10 | 9.8 ± 2.17 | 11.5 ± 2.46 |
| DLS (% Volume)[e] | 9.2 ± 2.36 | 7.9 ± 1.82 | 8.6 ± 1.77 | 8.6 ± 2.06 | 8.6 ± 2.08 | 10.2 ± 2.39 |
| DLS (% Number)[e] | 8.1 ± 1.82 | 7.2 ± 1.62 | 8.0 ± 1.57 | 7.8 ± 1.76 | 7.7 ± 1.76 | 9.2 ± 2.01 |

[a]Estimated edge-to-edge molecular length in fully extended structure.
[b]$pK_a$ values were calculated by ACD/PhysChem Suite, version 12.01, Advanced Chemistry Development, Inc., Toronto, ON, Canada.
[c]Contact angle of water on mica surfaces coated by QDs displaying each ligand. Std. Dev. <10% for all samples.
[d]Measured in 1x TBE buffer (pH 8.3).
[e]Due to diverse ways to represent data, the hydrodynamic diameters characterized by different profiles are shown here for comparison. Intensity profile is used for the present discussion.

The salt stability of the compact ligands was also examined. With 3.5 M NaCl in deionized water, the compact ligands CL1, CL2, and CL3 were found to be highly stable for at least 20 days, whereas DHLA acting as a ligand began to degrade within 16 hours.

Protein Conjugates

Recombinantly modifying proteins to express oligohistidine tags $(His_n)$ allows for metal-affinity interactions to bind the proteins to various metals, such as found on the surface of quantum dots. This capability may be used to, e.g., conjugate CdSe—ZnS QDs to an array of oligohistidine-appended proteins, peptides and even appropriately modified DNA to assemble a variety of QD bioconjugates for sensing, imaging and cellular probing applications.

It was evaluated whether $His_n$-mediated assembly could be achieved with the CL-QD series. Previous studies revealed that although smaller peptides can interact with many types of QDs via $His_n$-interaction, conjugation to proteins in the same manner required the use of QDs capped with short DHLA surface ligands, and was ineffective when PEG-based ligands were used. Stable conjugation between QDs and His-tagged proteins requires minimization of the steric hindrance caused by the surface ligands on the QDs, and it was found that the larger, globular nature of proteins combined with the steric hindrance of the long PEG chains on the QD surface prevents the His-tag from interacting directly with the metal-rich QD surface. However, as DHLA-capped QDs are stable only in basic buffers, this has severely limited effective use of DHLA-QD/$His_n$-protein conjugates. The CL series are expected to increase the chance that $His_n$-tags on proteins reach the QD surface and form stable binding interactions with it.

sembled to 550 nm emitting QDs capped with CL1, CL2 and CL4 at ratios of 0, 2 and 5 per QD. As CL3 is neutral, it was not tested in this configuration. QD-MBP-TR conjugates were then separated side-by-side with free MBP-TR in 1.5% agarose gels where use of filters allowed separate visualization of the QD and sensitized Texas Red emission bands on the gel using UV excitation. It was found that as the ratio of 5×His MBP-TR was increased, discrete slower moving bands appeared along with the higher mobility unconjugated QD bands for each of the CL-QD samples when observed with the 525 nm band-pass filter. The unconjugated QD front-moving band also visibly decreased in intensity with increasing MBP-TR. The Texas Red bands visualized with the 590 nm long-pass filter coincide with those of the slower moving QD-MBP conjugates. Changes in mobility of QD/MBP-TR conjugates are due to increases in relative mass/charge arising from assembly of MBP-TR onto the QD surface. In comparison, the slowest gel mobility was observed for unconjugated MBP-TR which also appears quite faint due to a low direct and unsensitized excitation in the UV. Colocalization of the QD and Texas Red emission, along with sensitization of the latter for co-assembled samples, confirm that the QDs and MBP-TR are indeed conjugated and migrating together.

Energy Transfer

Figure 4A:
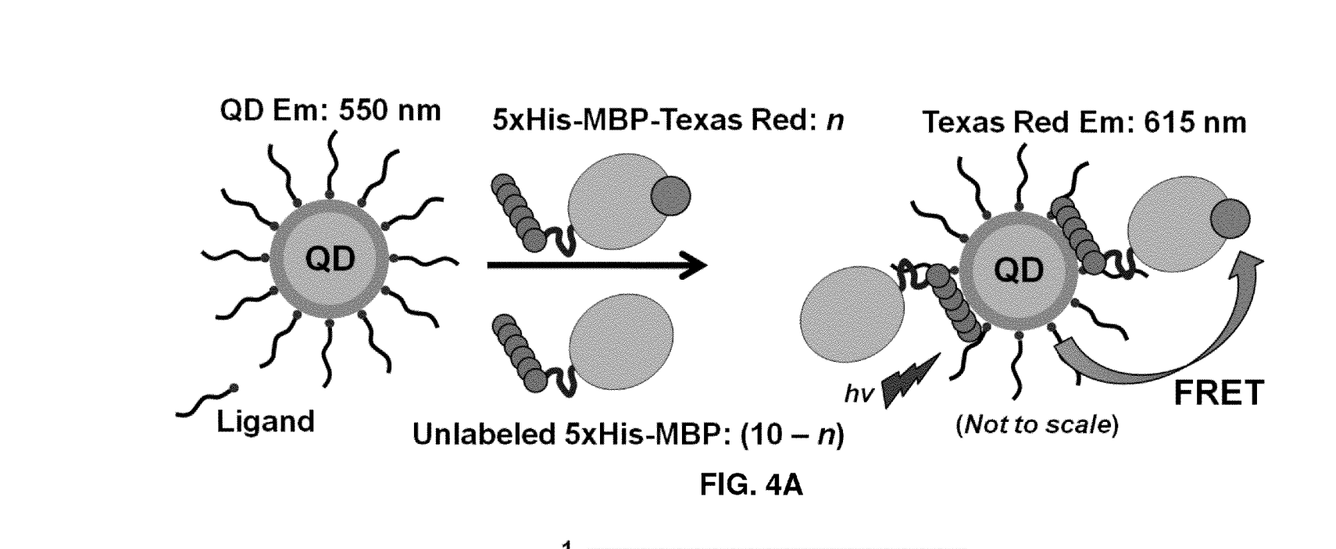
FIG. 4A is a schematic of a FRET (Förster resonance energy transfer) assay used to investigate direct assembly of His-tagged maltose binding protein (MBP) labeled with Texas Red (TR) onto QD surfaces.

Since the PL of 550 nm emitting QD and the absorption of Texas Red have a sizable spectral overlap (I(λ) of $2.98 \times 10^{-13}$ M⁻¹cm³ and Förster distance or $R_0$ of 45 Å), formation of the QD-MBP-TR conjugates was expected to facilitate an efficient level of energy transfer from the QD donor to the proximal Texas Red dye acceptor. FIG. 4A is a schematic of a FRET (Förster resonance energy transfer) assay used to investigate direct assembly of His-tagged MBP labeled with Texas Red onto QD surfaces.

It has been previously demonstrated that conjugation of His-tagged biomolecules onto QD surfaces commonly increases the fluorescence intensity or quantum yield of the QDs; this enhancement is ascribed to better passivation of surface trap states on the QD surface. Assembling unlabeled 5×His MBP onto the current CL-QD series resulted in similar changes further confirming His-tagged MBP binding to CL-functionalized nanocrystals. In order to effectively address PL enhancement caused by His-tagged protein binding onto QDs during the subsequent FRET analysis, the total amount of His-tag MBPs assembled was fixed at 10 equivalents per QD, while the discrete ratio of Texas Red-labeled (n) and unlabeled His-MBP (10-n) was systematically varied (n=0-to-10). This approach has been utilized previously and mitigates issues of changes in PL enhancement and the need for a more complex analysis to account for self-assembly heterogeneity at low ratios.

Figure 4B:
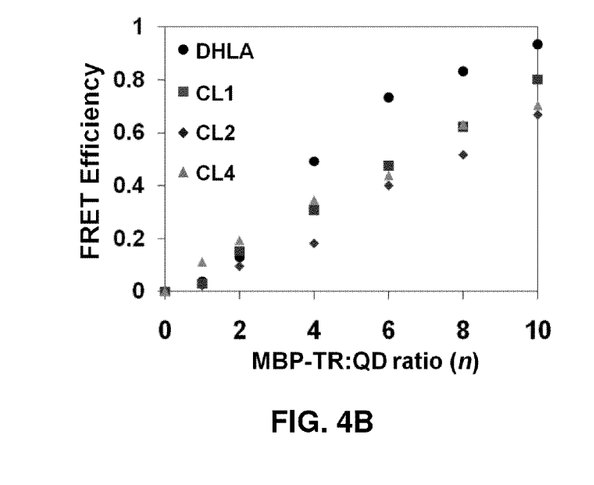
FIG. 4B shows FRET efficiencies from DHLA-, CL1-, CL2-, and CL4-QDs as a function of MBP-TR/QD ratio (n).

Spectra were collected from dispersions of the same CL-QD series as above incubated with MBP-TR at increasing ratios and excited at 400 nm where the absorption of Texas Red is minimal. DHLA-coated QDs were also measured as a positive control sample. As MBP-TR ratios increased, each QD/MBP-TR conjugate showed a decrease in QD PL concomitant with the appearance of a new fluorescence band at ~615 nm arising from Texas Red sensitization. The trends in these data sets closely mirrors that previously collected from a series of DHLA-capped QDs assembled with MBP labeled with Cy3-acceptor in the same 95C position. (Clapp, Medintz et al. 2004) FIG. 4B shows FRET efficiencies from DHLA-, CL1-, CL2-, and CL4-QDs as a function of MBP-TR/QD ratio (n). It is apparent that the described compact ligands are small enough to allow direct His-tag mediated conjugation of proteins onto the QD surface.

CL1 was further found to allow direct conjugation of a bulky protein (hexahistidine-tagged fluorescent mCherry protein) to the surface of a quantum dot, while maintaining stability (co-migration under gel electrophoresis) and achieving efficient Förster resonance energy transfer (FRET).

Moreover, the dye lissamine rhodamine B ethylenediamine (emitting at 592 nm) was successfully conjugated via EDC chemistry to quantum dots (emitting at 550 nm) coated with the described compact ligands. The quantum dots demonstrated efficient FRET, confirming the availability and reactivity of the carboxylic acid "chemical handle" of the compacts ligands as well as the dyes close proximity to the quantum dots.

Cellular Delivery

QDs coated with CLs were microinjected into the cytosol of COS-1 cells. Epifluorescence microscopy revealed that strong fluorescence existed throughout the cytosol with CL-coated QDs excluded from cellular nuclei, and that the coated QDs did not aggregate. Although the addressing of individual cells by this technique does not allow for full assessments of toxicity/viability (which was addressed by other experiments described below), cells appeared to be intact and visibly unperturbed for at least 6 h following injection. This suggests the availability of an experimental window for more complicated intracellular sensing experiments using this delivery mechanism. The excellent colloidal stability of these CL-QDs in the cellular environment is in marked contrast to DHLA-QDs, which exhibited punctate fluorescence under similar conditions, suggesting rapid aggregate formation and precipitation. It should be noted that while CL1, CL2, and CL4 were effective in the microinjection trials, attempts to microinject CL3-QDs failed with the nanocrystal samples appearing to precipitate at the cell-microinjector tip interface. It is possible that this is because, unlike the other ligands, CL3 lacks both a carboxyl and tertiary amine.

The use of peptides to facilitate delivery of CL-QDs was also examined. The cell penetrating peptide (termed "CPP") used herein has the sequence $R_9GGLA(Aib)SGWKH_6$. U.S. Patent Application Publication No. 2011/0097797 discloses additional peptides for cellular delivery of QDs and related background information. COS-1 cells were incubated for 1-2 h with either CL-QD-CPP assembled at 25 or 50 equivalents of CPP per QD, or control non-conjugated CL-QDs. It was found that self-assembly of CPP across the entire CL-QD series results in efficient cellular uptake of the conjugates. Punctate QD fluorescence was observed throughout the cytoplasm as well as in close proximity to the cell nuclei counterstained with DAPI. However, no nuclear staining by the QDs was apparent. Furthermore, there was no detectable fluorescence signal remaining on the plasma membrane, indicating a negligible degree of nonspecific binding of the CL-QD-CPP assemblies to the cells after washing. In contrast to the microinjection results, CL3-QD-CPP assemblies demonstrated very efficient delivery to the cells, as did CL1, CL2, and CL4. Co-localization of the CL-QD-CPP assemblies with labeled transferrin indicated that the uptake was via the endocytic pathway.

Cytotoxicity

The potential toxicity of delivering CL-QDs to cells was examined using a colorimetric tetrazolium-based cell proliferation assay which monitors the inhibition of cellular proliferation. Equivalent concentration ranges of CL-QD-CPP assemblies, unconjugated CL-QDs, and free CPP were exposed to the COS-1 cells under the same conditions used to deliver the peptides to cells. Following washing steps and a subsequent 72 h culture, no detrimental changes in proliferation for the CPP (tested up to 6.2 µM), unconjugated CL-QDs (tested up to 200 nM), or CL-QD-CPP assemblies (CPP:CL-QD ratio of 25:1, CL-QD tested up to 200 nM) relative to the untreated control were observed.

Compact Ligand-Functionalization of Gold Nanoparticles

The CL ligands were tested for applicability with gold nanoparticles (AuNPs). In contrast to the coating procedure used with the QDs, surface functionalization here does not require a reduction step to open the dithiolane ring, rather the thioctic amide derivatives of CLs (compounds 3, 6, 7, and 10 in FIGS. 2A-2D) are added in excess to citrate-stabilized AuNPs and the inherent gold-sulfur interactions open the dithiols during cap-exchange. Citrate-stabilized 5.8 nm AuNPs were cap-exchanged with the CL series along with DHLA. The CL-AuNPs were then subjected to a battery of the same characterization tests as the CL-QD series. Gel electrophoresis was used to verify that the ligands would impart similar surface charge/mobility characteristics to the AuNPs. It was seen the CL-AuNPs have an almost identical gel migration pattern as CL-QDs when compared to DHLA-AuNPs, suggesting that almost the same relative surface-charge properties are imparted to these materials. The hydrodynamic diameters of the 5.8 nm AuNPs coated with CL1-CL4 ranged from 12.1 to 13.9 nm. These values are comparable within error to the 13.2 nm measured for the same AuNPs coated with DHLA and are much smaller than those functionalized with DHLA-PEG750-COOH (17.3 nm). These trends are quite similar to the results collected from the QDs above. It was further found that the CLs also provided the AuNPs with a similar colloidal stability over time.

To verify that the carboxyl groups on the CL series would also be available for subsequent chemical modification, similar EDC coupling reactions were performed with a Cy3 dye-labeled peptide that had a particular lysine-amine within its sequence. CL4-AuNPs were reacted with increasing concentrations of excess dye-labeled peptide and then separated on a 1.5% agarose gel. The results confirm that the dye-labeled peptide could be conjugated to the AuNPs.

Compact Ligands with a 1,3,5-Triazine Scaffold

In addition to the compact ligands described above having central scaffolds of the form other compact ligands have been prepared using a central scaffold of 1,3,5-triazine, providing similar function while maintaining a desirably compact form.

FIG. 5 illustrates embodiments of compact ligands comprising a central 1,3,5-triazine scaffold derived from cyanuric chloride, wherein the depicted modules $Nu_1$, $Nu_2$, and $Nu_3$ replace the chloride atoms. Such ligands were prepared and found to have the desired zwitterionic properties and ability to coat nanoparticles. These ligands may be designed to have either one anchoring group and two functional arms per molecule (as with exemplary ligands B1 and B2 seen in FIG. 5), or two anchoring groups and one functional arm per molecule (as with exemplary ligands B3 and B4 seen in FIG. 5).

Embodiments of such ligands with two functional may have the same or different conjugation chemistry, thus providing numerous possibilities for chemical modification. Embodiments having two anchoring groups are expected to have improved stability when conjugated with a nanoparticle.

Compact Ligands with a Catechol Moiety

A catechol moiety may serve as an anchoring module in place of the above-described thioctic acid or dihydrolipoic acid groups, thereby providing binding to different types of nanoparticles. In particular, it is expected that catechol may facilitate binding to metal oxide nanoparticles. In embodiments employing catechol, the catechol is preferably at a terminal position, joined to the chemical backbone via a spacer having a length of 2, 3, 4, 5, 6, 7, or 8 carbon atoms.

Further Embodiments

In addition to the anchoring modules described above, one of ordinary skill in the art could envision other anchoring modules such as peptides or other chemical groups to target various materials.

In addition to nanoparticles, a great many of the compact ligands described herein could attach to surfaces (including planar and curved surfaces) such as surfaces comprising ZnS, gold, or metal oxide, thereby providing desirable properties such as anti-fouling.

Moreover, carboxymethyl and 3-sulfopropyl groups may be used potential substituents, attaching to the amino groups of the described backbones.

General

The ligands disclosed herein preferably provide the following characteristics to a nanoparticle-ligand dispersion, the combination of which is lacking in previously described ligands:

(1) Aqueous solubility
(2) Biocompatibility
(3) Small, molecular weight of less than about 400 to 500 Daltons
(4) Small hydrodynamic size of the nanoparticles coated by the compact ligands
(5) High affinity for nanoparticles surfaces, including metallic surfaces
(7) A chemical "handle" for chemical functionalization (e.g., COOH)
(8) Ability to synthesize ligand with different chemical handle (e.g., primary amine)
(9) Ability to synthesize ligand with more than one chemical handle
(10) Ability to synthesize ligand that cannot be further modified and is chemically inert
(11) Broad pH stability
(12) Tolerance against high ionic strength
(13) Modular design
(14) Little or no toxicity

Each and every document cited in this disclosure is incorporated herein by reference in its entirety.

All numbers expressing quantities of ingredients, constituents, reaction conditions, and so forth used in the specification are to be understood as being modified in all instances by the term "about." Notwithstanding that the numerical ranges and parameters set forth, the broad scope of the subject matter presented herein are approximations, the numerical values set forth are indicated as precisely as possible. Any numerical value, however, may inherently contain certain errors resulting, for example, from their respective measurement techniques, as evidenced by standard deviations associated therewith.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed in accordance with 35 U.S.C. §112, ¶6 unless the term "means" is expressly used in association therewith.

What is claimed is:

1. A composition comprising:
a compound is selected from the group consisting of wherein (A) is either wherein each respective dashed line represents an amide bond, and wherein (B) and (C) are each independently selected from the group consisting of 2-hydroxyethyl, 3-carboxypropyl, 2-carboxyethyl, 2-aminoethyl, and 2-sulfoethyl.

2. The composition of claim 1, further comprising a nanoparticle coated with said compound.

3. The composition of claim 2, wherein:
(a) said nanoparticle is a quantum dot or a metallic nanoparticle;
(b) further comprising a cell penetrating peptide attached to the nanoparticle;
(c) said nanoparticle coated with said compound has a hydrodynamic diameter of less than 10 nm; or
(d) two or more of (a), (b), and (c).

4. The composition of claim 1, wherein said compound comprises both a carboxyl group and a tertiary amine.

5. The composition of claim 1, wherein said compound is selected from the group consisting of and

6. The composition of Claim 1, wherein said compound is selected from the group consisting of and -continued

7. The composition of claim 1, wherein the compound is zwitterionic from pH 4 to pH 13.

8. A method of modifying a nanoparticle, the method comprising contacting the nanoparticle with a compound according to claim 1.

9. The method of claim 8:
(a) wherein said nanoparticle is a quantum dot or a metallic nanoparticle;
(b) further comprising attaching a cell penetrating peptide to the nanoparticle; or
(c) wherein said compound according to claim 1 comprises both a carboxyl group and a tertiary amine.

10. The method of claim 8, wherein said compound is selected from the group consisting of and

11. The method of claim 8, wherein said compound is selected from the group consisting of 12. The method of claim 8, wherein said nanoparticle coated with said compound has a hydrodynamic diameter of less than 10 nm.

* * * * *